United States Patent [19]

Forte

[11] Patent Number: 5,108,451
[45] Date of Patent: Apr. 28, 1992

[54] FEMORAL COMPONENT OF A HIP JOINT PROSTHESIS

[76] Inventor: Mark R. Forte, 11 Oak La., Pine Brook, N.J. 07058

[21] Appl. No.: 648,599

[22] Filed: Jan. 31, 1991

[51] Int. Cl.$^5$ ............................................. A61F 2/34
[52] U.S. Cl. ................................................. 623/23
[58] Field of Search ..................... 623/16, 18, 19, 20, 623/22, 23

[56] References Cited

U.S. PATENT DOCUMENTS

| | | | |
|---|---|---|---|
| 4,287,617 | 9/1981 | Tornier | 623/23 |
| 4,783,192 | 11/1988 | Wroblewski et al. | 623/23 |
| 4,957,510 | 9/1990 | Cremascoli | 623/23 |

Primary Examiner—David Isabella
Attorney, Agent, or Firm—Klauber & Jackson

[57] ABSTRACT

A system of three femoral components with the same distal diameter, for a hip joint prosthesis, includes an intramedullary stem for each femoral component, each stem having a distal end, a proximal end, a lateral side extending between the distal and proximal ends, and a medial side extending between the distal and proximal ends opposite to the lateral side, the medial side at a proximal portion of the stem having a concave curvature; a neck mounted to the proximal end of each stem; a femoral ball component mounted at the proximal end of each neck, each femoral ball component having an articular center; the medial sides at the proximal portions of all of the stems substantially being in exact alignment only when the intramedullary stems are offset in the lengthwise direction from each other, thereby permitting a consistent fit within a given femur and achieving different positions of the articular centers of the femoral ball components, since the medial sides at the proximal ends of all of the stems are given distal diameter have the same radius of curvature, and with the stems incorporating the same proximal-medial radius of curvature for a given distal diameter reflecting consecutive larger proximal-transverse stem widths for addressing a consistent, light mechanical press-fit into femurs of different physiological sizes.

13 Claims, 6 Drawing Sheets

| D | mm | 7 | 8 | 9 | 10 | 11 | 12 | 13 | 14 | 15 |
|---|---|---|---|---|---|---|---|---|---|---|
| R | in. | 4.70 | 4.76 | 4.84 | 4.95 | 5.06 | 5.22 | 5.46 | 5.78 | 6.10 |
|   | mm | 119 | 121 | 123 | 126 | 129 | 133 | 139 | 147 | 155 |

FEMORAL COMPONENT OF A HIP JOINT PROSTHESIS

BACKGROUND OF THE INVENTION

This invention relates generally to a femoral component of a hip joint prosthesis and, more particularly, is directed to the shape of the intramedullary stem which is inserted into the surgically prepared medullary canal of the proximal femur for fixation or anchorage of the prosthesis into the surrounding supportive cortical bone.

As is well-known in the art, the intramedullary stem or blade-like portion of the femoral component of a hip joint prosthesis is inserted into the prepared medullary canal of the proximal femur for fixation within the surrounding bone structure. This fixation occurs by either a bone cementing means which employs methyl methacrylate, or by a biological fixation means employing a mechanism of bone ingrowth within minute voids or porosities of a specially applied porous-like metal alloy surface structure This porous surface structure is metallurgically integrated onto the surface of the prosthesis stem at specially selected locations.

With this in mind, consistency or congruency of the shape of the femoral prosthesis stem, relative to the shape of the proximal medullary canal of the femur, is an important technical and clinical consideration for achieving a more uniform mantle thickness of interposed affixing bone cement which tends to maintain improved uniformity of the developed stresses under functional loading when a bone cement fixation means is employed and for achieving a tight mechanical press-fit of the intramedullary stem portion of the femoral component prosthesis within the adjacent supporting bone structure of the proximal medullary canal when a biological bone ingrowth fixation means is employed It is also known that a tight mechanical press-fit between the femoral prosthesis stem and adjacent bone provides the necessary prerequisites for achieving clinically reliable bone ingrowth fixation, namely, by providing close interface apposition of the adjacent bone with the porous structure of the prosthesis for considerations of enhanced bone ingrowth mechanics and by providing the mechanical stability to preclude significant micromotion at the bone/porous coating interface during the prolonged post-operative bone ingrowth period. The occurrence of interface micromotion is generally considered as a major deterrent for achieving bone ingrowth fixation and is a contributing factor in clinical failures associated with femoral prosthesis loosening.

Unfortunately, due to the wide variety of femurs, and more specifically, the shape of the proximal intramedullary canal from physiological size variations, as well as disease, trauma and congenital related factors, achieving a consistent tight and reliable pressfit of the prosthesis stem within the available adjacent bone structure of the proximal femur, without resorting to significant bone preparation sculpturing (if sufficient bone mass is available), is generally a difficult surgical accomplishment, requiring careful attention to surgical detail.

Many contemporary hip prosthesis femoral components, such as those described in U.S. Pat. Nos. 4,551,863; 4,840,632; 4,851,007; 4,908,035; 4,919,678; and 4,936,863 incorporate a straight, intramedullary stem design in the lateral view or anterior-posterior (A-P) plane. In this plane, the straight intramedullary stem of the femoral prosthesis component is seated and stably positioned within the curved proximal femur by selecting a stem of proper distal intramedullary stem diameter or distal size which is consistent with distal reaming to allow a three-point support by adjacent bone structure Attainment of a more complete stem fit in the lateral view or anterior-posterior plane of the proximal femur is technically difficult, due to the characteristic serpentine shape of the medullary canal in this plane. The shape of the proximal femur in the A-P view or medial-lateral plane is consistent with accepted means of canal preparation, that is, distally reaming the cortical bone, and also reaming the cancellous bone proximally-laterally, as well as rasping the cortical and cancellous bone proximal-medially. Additionally, the convergent shape of the medullary canal in the A-P view (M-L plane) not only facilitates surgical preparation of the medullary canal but also facilitates prosthesis stem insertion and achievement of a tight stem press-fit. The medullary stem of the femoral prosthesis should attain an exact fit with the endosteal surfaces of the proximal canal, as viewed in an A-P radiograph and the attainment of a three-point stem support in the lateral radiograph. The medial and lateral borders of the stem should intimately contact adjacent bone surfaces, along the entire medullary stem length, with minimal interface gaps, reflective of a tight and mechanically stable press-fit.

Of course, proper surgical technique and careful attention to detail in the preparation of all bony surfaces, relative to the geometric shape and dimensional size of the femoral prosthesis stem, must be carefully considered both preoperatively and at surgery to avoid inadvertent bone fracture upon attempted seating of the prosthesis.

Additionally, besides attempting to achieve a stable mechanical press-fit within the proximal femoral canal for the porous ingrowth fixation mode (and for the cemented mode, as well), the surgeon must attempt to position the center of the bearing head of the femoral prosthesis coincident with the articular center of the hip joint for duplication of the natural functional biomechanical characteristics of the hip. The two principal spacial components of femoral head position include vertical off-set distance (vertical elevation from the collar or neck resection level to the head center) for leg length considerations and horizontal offset (horizontal dimension between the medullary stem center-line and the head center) for attainment of proper hip joint function and power characteristics.

Some variability of femoral head position is generally provided to the surgeon by selection of a range of modular neck lengthening prosthesis head components which allow discrete incremental increases in both the vertical and horizontal off-sets. Variation in just a horizontal component of the femoral head position is achieved by selecting an alternative femoral component design, which incorporates a larger horizontal off-set. This may not be readily available for a given distal stem size within the same prosthesis system, and accordingly, may involve consideration of a long lead-time custom device, or more probably, consideration of another prosthesis system alternative may have to be explored. Variation in just the vertical femoral head off-set can be achieved by preparing the proximal femoral canal to accept the prosthesis at a higher position or by selecting an alternative femoral component design of proper distal diameter, but with a broader proximal-transverse or proximal medial-lateral (M-L) intramedullary stem width, allowing the prosthesis to seat at a higher position within the femur. The former technique for seating the femoral component at a higher position can result in larger stem/bone interface gaps proximal-medially, a condition reflective of a less desirable, and possibly less stable, stem fit. Conversely, to lower the vertical head off-set position, a femoral prosthesis stem of narrower proximal-transverse width can be employed, which allows the prosthesis to seat at a lower position within the femur. Lower prosthesis seating may also result in an inexact fit between the stem and bone, especially if the femur was surgically prepared for a larger proximal stem design of different proximal-medial curvature. Again, these adjustments in femoral head position must be surgically achieved while coincidentally attaining a tight, stable intramedullary stem fit within the proximal femur with minimal interface gaps between the stem and bone.

The attainment of a tight stem/bone fit is difficult to verify interoperatively, although some techniques of somewhat limited and questionable utility currently exists. For a good, reliable press-fit, there is no substitute for extensive surgical experience, exacting preoperative planning and design sensibility and consistency-between the shape of the intramedullary stem, the shape of the proximal medullary canal and the surgical instrumentation for preparing and shaping the femur bone bed to accept the prosthesis.

Still another prosthesis sizing consideration involves the variation of the proximal femoral transverse canal size relative to a given distal canal diameter and given femoral head position. Few contemporary prosthesis systems are designed to directly accommodate this commonly encountered dimensional canal variation. This situation is usually indirectly accommodated by inserting a proximally undersized or oversized prosthesis stem to achieve a so-called press-fit, and managing resultant lower or higher medullary stem position by selection of a modular neck length component for attainment of proper leg length adjustment, while accepting whatever horizontal femoral head off-set that results.

Still another stem sizing consideration involves the geometric curvature or shape of the proximal-medial intramedullary stem. It appears that many of currently available femoral prosthesis systems claim that the respective stem design is "physiologically" configured to achieve a consistent and mechanically stable "press-fit". However, all appear to reflect different geometric configurations and correspondingly, different levels of physiological conformity with the proximal femoral canal, when tested in a typical preoperative planning setting.

OBJECTS AND SUMMARY OF THE INVENTION

Accordingly, it is an object of the present invention to provide a system of femoral components that overcomes the aforementioned problems.

It is another object of the present invention to provide a system of femoral components that achieves a consistent intramedullary stem fit with variations of femoral canal size and shape usually encountered clinically.

It is still another object of the present invention to provide a system of femoral components that provides acceptable positional duplication of the biomechanical center of the patient's reconstructed hip joint.

It is yet another object of the present invention to provide a system of femoral components in which the same distal bore in the femur can accommodate a plurality of intramedullary stems of different proximal-transverse size with an exact fit, while obtaining different head center positions.

It is a further object of the present invention to provide a system of femoral components having the same medial curvature for a given distal stem size.

It is a still further object of the present invention to provide a system of femoral components having proximal-medial stem curvature which conforms more precisely to the medial curvature of the proximal femur and which physiologically relates to the size of the distal femoral canal.

It is a yet further object of the present invention to provide a system of femoral components in which the instrumentation design is reduced to a singular rasp for each distal size of femur, and thereby reducing the total number of instruments required.

It is another object of the present invention to provide a system of femoral components in which manufacture thereof is simplified because the number of patterns required to generate the different shapes can be accommodated by a single shape for each distal stem size and similarly any machining processes require only a single nesting fixture per distal stem size.

In accordance with an aspect of the present invention, a system of femoral components for a hip joint prosthesis, includes an intramedullary stem for each femoral component, each stem having a distal end, a proximal end, a lateral side extending between the distal and proximal ends, and a medial side extending between the distal and proximal ends opposite to the lateral side, the medial side having a concave curvature; a femoral ball component mounted at the proximal end of each stem, each femoral ball component having an articular center; and the medial sides of at least two other stems substantially being in exact alignment only when the stems are offset in the lengthwise (proximal-distal) direction from each other, thereby coincidentally permitting identical proximal-medial stem curvature and different positions of the articular center of the femoral ball components.

The above and other objects, features and advantages of the present invention will become readily apparent from the detailed description thereof which is to be read in connection with the accompanying drawings.

DETAILED DESCRIPTION OF A PREFERRED EMBODIMENT

Figure 1A:
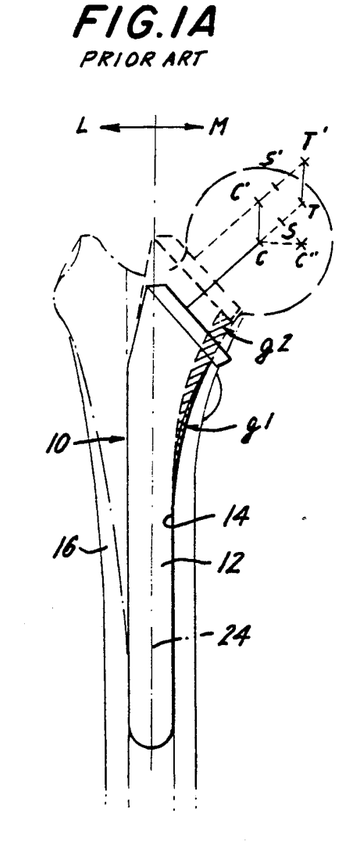
FIG. 1A is a front or anterior elevational view of an intramedullary stem of a known femoral prosthesis component mounted in the femur, and taken within the medial-lateral plane, similar to an A-P X-ray view.

Referring to the drawings in detail, and initially to FIG. IA, a femoral component 10 according to the prior art includes an intramedullary stem 12 which is inserted within the prepared medullary canal 14 of a femur 16 for fixation within the surrounding bone structure by a biological fixation means, as aforementioned. Femoral component 10 further includes a neck (not shown) and a ball component (not shown), as is conventional.

Figure 1B:
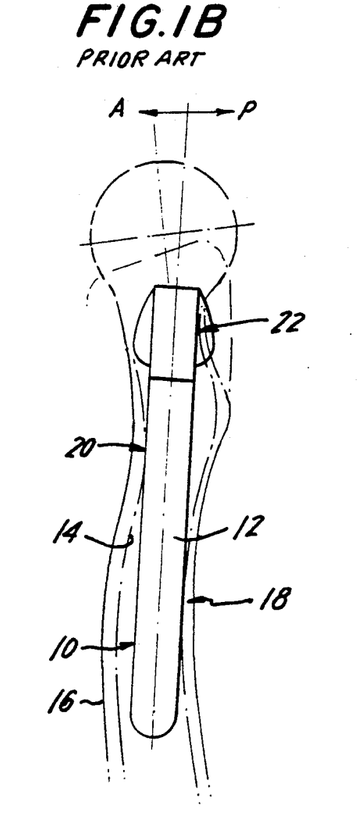
FIG. 1B is a lateral side elevational view of the intramedullary stem of FIG. 1A, taken within the anterior-posterior plane, similar to a lateral X-ray view.

As shown in the anterior-posterior (A-P) plane or lateral view of FIG. IB, the size or diameter of the straight intramedullary stem 12 of femoral component 10 is selected to permit a three-point support at points 18, 20 and 22 by adjacent bone structure. However, the attainment of a more complete stem fit in the anterior-posterior (A-P) plane or lateral view of the proximal femur is technically difficult due to the characteristic serpentine shape of medullary canal 14. The shape of the proximal femur in the medial-lateral (M-L) plane or A-P view is consistent with accepted means of canal preparation, that is, distal reaming of the cortical bone and proximal-lateral reaming of cancellous bone, as well as proximal-medial rasping of cortical and cancellous bones. Additionally, the convergent shape of medullary canal 14 in the A-P view not only facilitates surgical preparation of medullary canal 14, but also facilitates prosthesis stem insertion and achievement of a tight stem press-fit. In such case, intramedullary stem 12 should attain an exact fit with the endosteal surfaces of the proximal canal in the medial-lateral plane as viewed in FIG. 4A and the attainment of the aforementioned three-point stem support in the anterior-posterior plane as viewed in FIG. 1B.

Figures 4A, 4B, 4C:
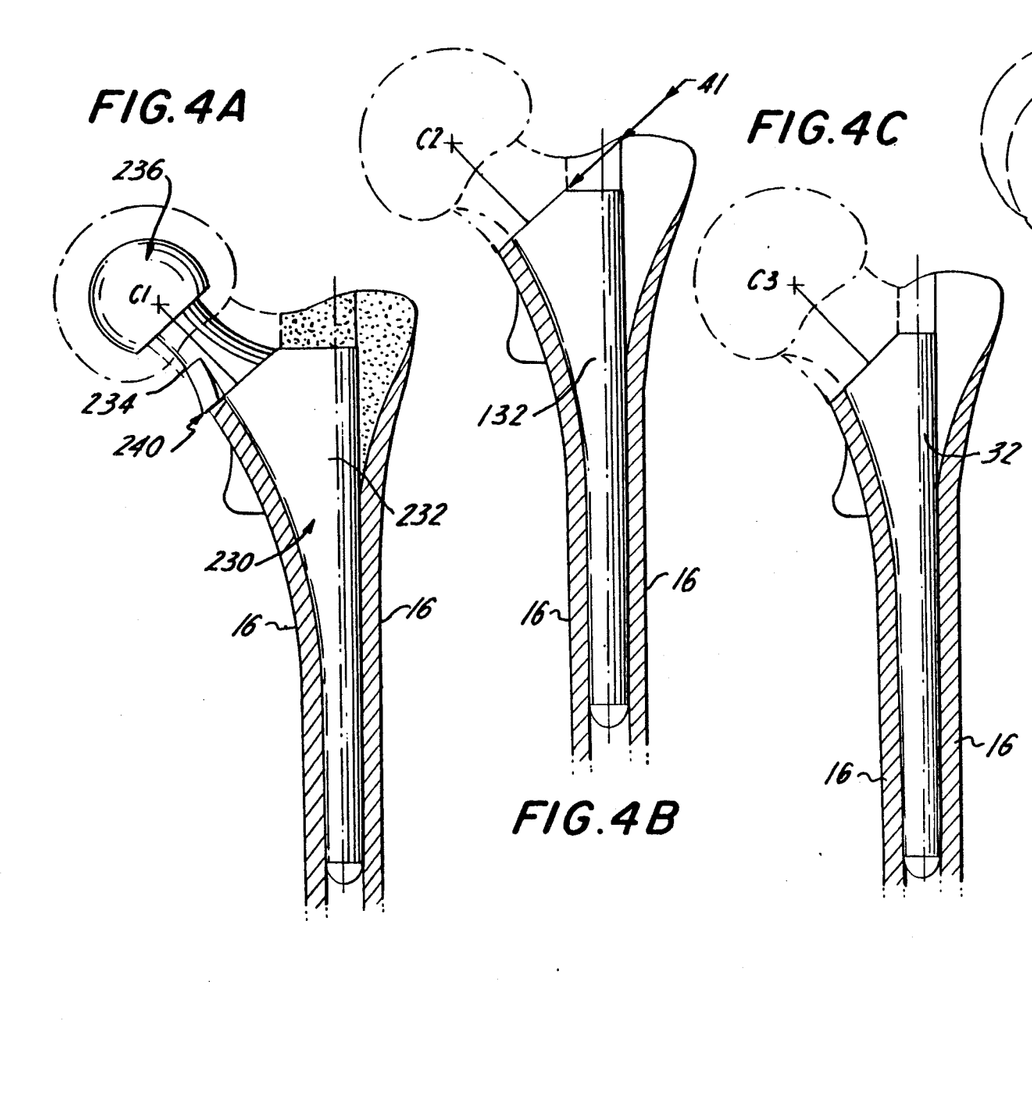
FIG. 4A is an anterior elevational view of the first (left-side) femoral prosthesis component of FIG. 3A mounted in a femur.
FIG. 4B is an anterior elevational view of the second (middle) femoral prosthesis component of FIG. 3A mounted in a femur.
FIG. 4C is an anterior elevational view of the third (right-side) femoral prosthesis component of FIG. 3A mounted in a femur.

The medial and lateral borders of the stem should intimately contact adjacent bone surfaces, along the entire medullary stem length, with minimal interface gaps, as shown in FIG. 4A, so as to be reflective of a tight and mechanically stable press-fit.

Additionally, besides attempting to achieve a stable mechanical press-fit within the proximal femoral canal for the porous ingrowth fixation mode, the surgeon must attempt to position the bearing head or ball of the femoral prosthesis coincident with the articular center C (FIG. 1A) for duplication of the natural functional biomechanical characteristics of the hip joint.

As discussed previously, the two principal spacial components of femoral head position include vertical off-set distance which is the vertical elevation from the collar or neck resection level to the head center C for leg length considerations and horizontal off-set which is the horizontal dimension between the medullary stem center-line 24 and head center C for attainment of proper hip joint function and power characteristics.

Some variability of femoral head position is generally provided to the surgeon by selection of a range of modular neck lengthening prosthesis head components which allow discrete incremental increases in both the vertical and horizontal off-sets, as shown by points C, S and T in FIG. 1A. Variation in just the horizontal component of the femoral head position, such as shown by point C" in FIG. 1A is achieved by selecting an alternate femoral component design, which includes a larger horizontal offset. However, this may not be readily available for a given distal stem size within the same prosthesis system, and accordingly, may involve consideration of a long lead-time custom device, or more probably, consideration of another prosthesis system. Variation in just the vertical femoral head off-set is shown from points C, S and T to points C', S' and T', respectively, in FIG. 1A. This can be achieved by preparing the proximal femoral canal to accept the prosthesis at a higher position or by selecting an alternative femoral component design of proper distal diameter, but with a broader proximal-transverse (M-L) intramedullary stem width which allows the prosthesis to seat at a higher position within femur 16.

However, the technique for seating the femoral component at a higher position can result in larger gaps in the vicinity of the proximal-medial stem portion, as shown by the larger gap G2 in comparison with gap G1 in FIG. 1A, which can produce a resultant less desirable, and possibly less stable, stem fit.

Conversely, to lower the vertical head off-set position, a femoral prosthesis stem of narrower proximal-transverse width can be employed, which allows the prosthesis to seat at a lower position within the femur. However, lower prosthesis seating may also result in an inexact fit between the stem and bone, particularly if the femur was surgically prepared for a larger proximal stem design of different medial curvature. However, these adjustments in the femoral head position must be surgically achieved while coincidentally attaining a tight, stable intramedullary stem fit within the proximal femur 16 with minimal gaps between the stem and bone. The attainment of a tight stem/bone fit is difficult to verify interoperatively, although some techniques of somewhat limited and questionable utility currently exist. For a good and reliable press-fit, there is no substitute for extensive surgical experience, exacting pre-operative planning and design sensibility and consistency between the shape of intramedullary stem 12, the shape of the proximal medullary canal 14 and the surgical instrumentation for preparing and shaping the bone bed to accept the prosthesis.

Figure 1C:
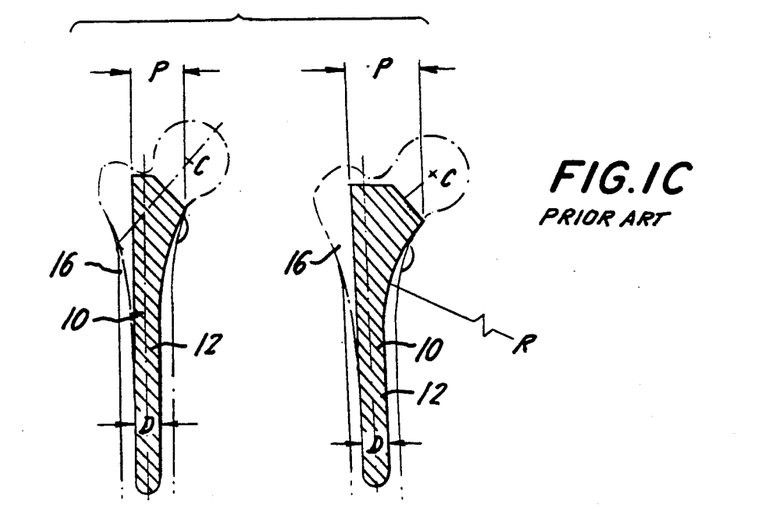
FIG. 1C shows two different intramedullary stems according to the prior art with different proximal widths, taken in cross-section in the medial-lateral plane.

As further discussed, another prosthesis sizing consideration involves the physiological variation of the proximal-transverse femoral canal size P relative to a given distal canal diameter D and given femoral head position C, as shown in FIG. 1C. Few contemporary prosthesis systems are designed to directly accommodate these commonly encountered dimensional canal and head offset variations. This situation is usually indirectly accommodated by inserting a proximally undersized or oversized prosthesis stem to achieve an intramedullary press-fit and managing the resultant lower or higher medullary stem position by selection of a modular femoral head component for attainment of proper leg length adjustment, thereby accepting whatever horizontal femoral head off-set that results.

Referring now to FIGS. 2A-2E, a femoral prosthesis component 30 according to one embodiment of the present invention includes an intramedullary stem 32 having a straight stem design relative to the A-P plane or lateral view. Femoral component 30 further includes a neck 34 extending from the proximal end of intramedullary stem 32 and a femoral head or ball component 36 mounted to the free end of neck 34.

Figure 2:
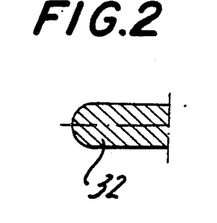
FIG. 2A is an anterior or posterior elevational view of a femoral prosthesis component according to the present invention, viewed in the medial-lateral plane.
FIG. 2B is a lateral side elevational view of the femoral prosthesis component of FIG. 2A, viewed in the anterior-posterior plane.
FIG. 2C is a cross-sectional view of the femoral prosthesis component of FIG. 2A, taken along line 2C—2C thereof.
FIG. 2D is a cross-sectional view of the femoral prosthesis component of FIG. 2A, taken along line 2D—2D thereof.
FIG. 2E is a cross-sectional view of the femoral prosthesis component of FIG. 2A, taken along line 2E—2E thereof.
Figure 2A:
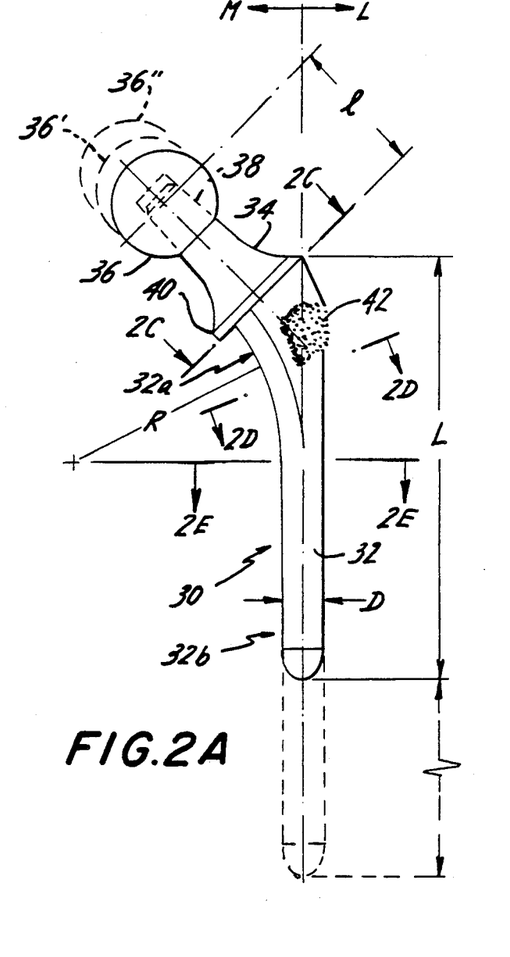
Figure 2B:
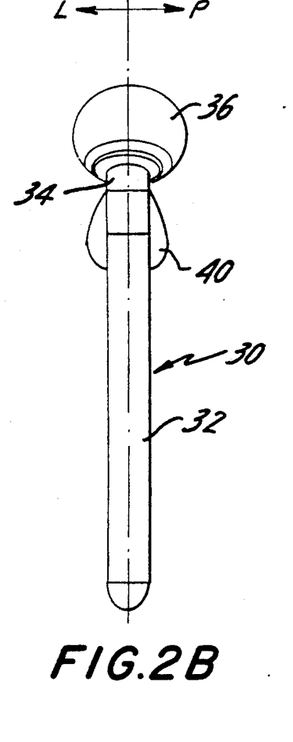
Figure 2D:
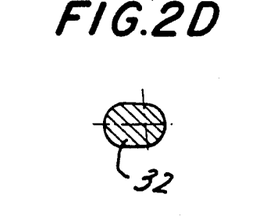

Femoral head 36 is modular in that a variety of head 35 components at different positions 36, 36' or 36" can be selected with varying neck lengths 1 and assembled onto a locking Morse taper connection 38 on the proximal portion of neck 34.

Femoral neck 34 is integral with a collar portion 40 that is interposed between stem 32 and neck 34. Collar portion 40 is designed to maintain contact with the femur bone at the level of the femoral neck resection 41 (FIG. 4b) and to provide axial support of femoral prosthesis component 30. Collar portion 40 is integral with intramedullary stem 32 which is inserted and affixed within the medullary canal of the proximal femur.

Further, the proximal portion 32a and/or the distal portion 32b of stem 32 may incorporate a metal alloy porous surface structure 42, which is metallurgically bonded to the substrate of stem 32. Porous structure 42 enhances the fixation bond within the femoral canal when a bone cement fixation means is employed, and also provides the porous structure into which bone can invade and grow for a biological stem fixation means.

Preferably, femoral prosthesis component 30, including femoral head 36, are fabricated of either cobalt-chrome alloy or 6A14V-ELI titanium alloy. The respective porous surface structure is formulated either of cobalt-chrome alloy or CP and/or 6A14V titanium alloy, which is either sinter bonded, diffusion bonded or flame sprayed onto the substrate surface.

Figure 3A:
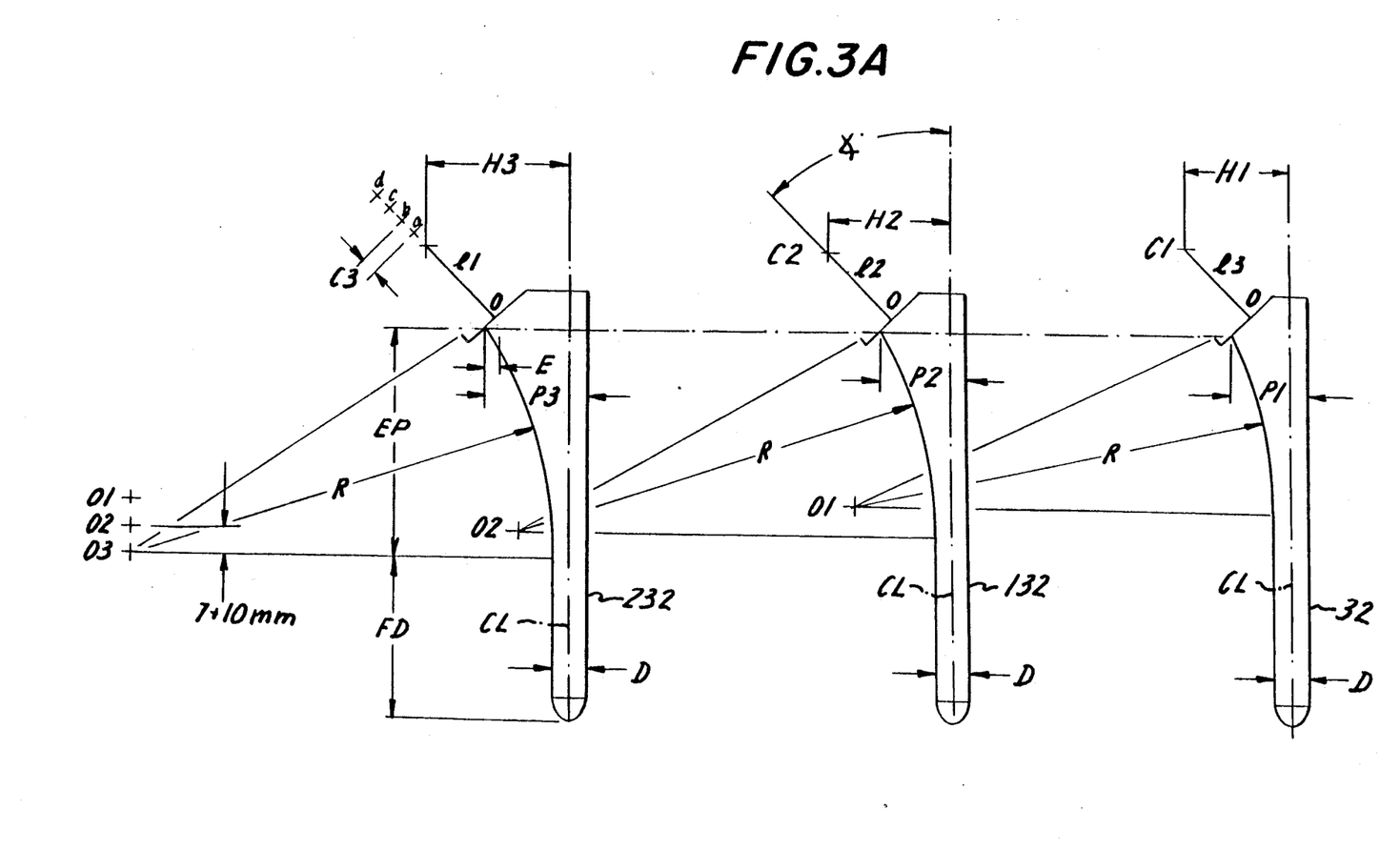
FIG. 3A is an anterior or posterior elevational view of a system of three intramedullary stems according to the present invention.

In accordance with the present invention, and as shown best in FIG. 3A, the system according to the present invention utilizes a plurality of stem sizes, shown by intramedullary stems 32, 132 and 232. For a given distal stem diameter D, stem 32 has a proximal-transverse width P1; stem 132 has a proximal-transverse width P2; and stem 232 has a proximal-transverse width P3. As an object of the present invention, stems 32, 132 and 232 can be accommodated into different proximal femoral bone geometries with identical distal diameters D to address the physiological differences of different femurs, that is, the physiological variations of proximal femoral canal shape associated with male, female and CDH hips, as well as disease and trauma-related differences. For example, stem 232 is for use with a male patient; stem 132 is for use with a female patient; and stem 32 is for use with congenital deformed (CDH) patients. It will be appreciated that a set of three stems having different proximal transverse widths can be produced for different distal stem diameters D. For example, a set of three stems can be provided for distal stem diameters at one mm increments from about a 7 mm diameter to about a 20 mm diameter. In this regard, it will be appreciated that the stem length L (FIG. 2A) can be proportional to the distal diameter D and preferably ranges from about 110 mm to about 200 mm, although longer or shorter stem lengths can be fabricated, relative to the individual requirements of the patient, when required.

In accordance with an important aspect of the present invention, for each set of stems 32, 132 and 232, the proximal-medial curvature of the intramedullary stem of given distal diameter D is defined by the same radius of curvature R for all three proximal stem widths P1, P2 and P3. However, the origins 01, 02 and 03 of the radii of curvature R for stems 32, 132 and 232 are displaced along the proximal-distal direction, separated by a distance m of approximately 7-10 mm, depending upon the overall stem distal diameter D, as shown in FIG. 3A. As the origin 03 of the radius of curvature R moves proximally to origins 02 or 01 for stems 132 or 32, the resultant transverse stem width decreases by dimension E, and hence, results in a decrease in the proximal stem width from P3 to P2 to P1, respectively.

Figure 3B:
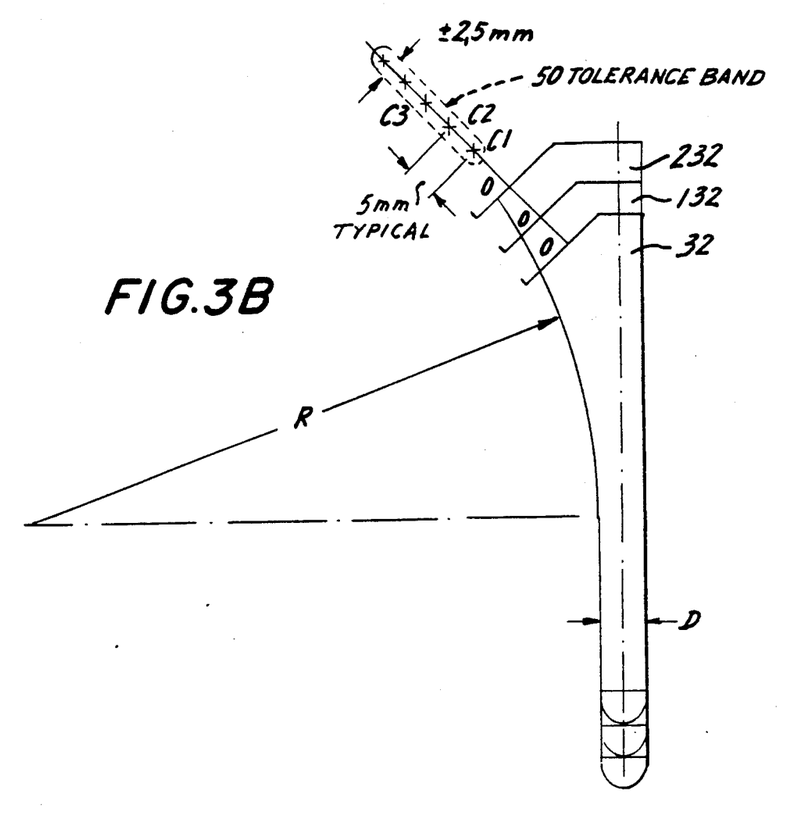
FIG. 3B is an anterior or posterior elevational view of the three intramedullary stems of FIG. 3A, superimposed upon each other; showing the head centers offset from each other in the vertical and horizontal directions.
Figure 3C:
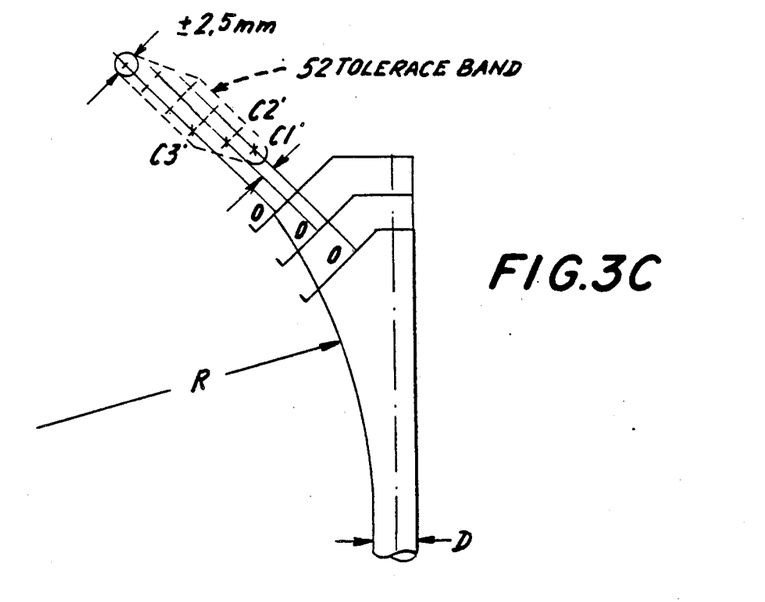
FIG. 3C is an anterior or posterior elevational view of a portion of three intramedullary stems according to the present invention, showing the head centers offset from each other in the vertical and horizontal directions.
Figure 3D:
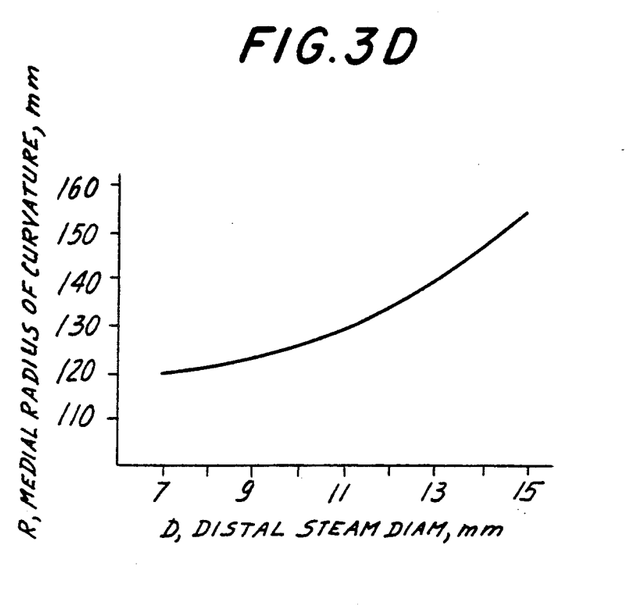
FIG. 3D is a graphical plot of the medial stem radius of curvature versus the distal stem diameter according to the present invention.
Figure 3E:
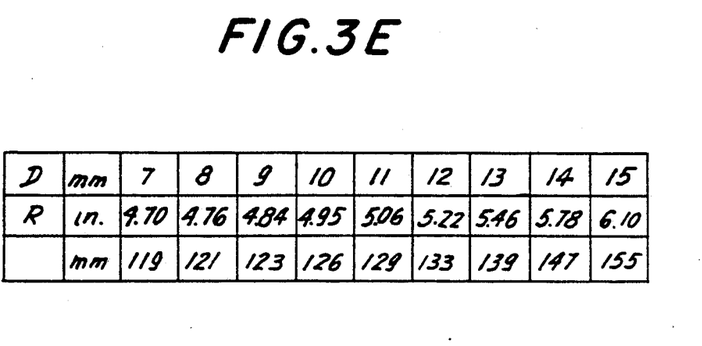
FIG. 3E is a chart showing the numerical data for plotting the graph of FIG. 3D.

The variation of the radius of curvature R as a function of distal diameter D is plotted in FIG. 3D. These values (FIG. 3E) were empirically obtained from A-P X-rays of Japanese patients and tested on additional X-rays of other patients to verify an excellent and consistent stem fit and conformity with proximal-medial shape of the femoral medullary canal.

Figure 2E:
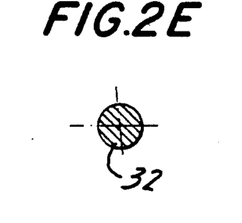

In all of the stems 32, 132 and 232, the distal portion thereof, which is preferably of a cylindrical or circular cross-sectional configuration, as shown in FIG. 2E, although a tapered design can also be selected if clinically warranted, originates at the identical level, that is, transversely opposed to the origin 01, 02 or 03 of the radius of curvature R, as shown in FIG. 3A and oriented perpendicular to the center line CL of the medullary stem. In this regard, the distal stem length is shown in FIG. 3A as FD with respect to stem 232 and the proximal stem length is shown as FP in FIG. 3A with respect to stem 232. The terminus of the distal stem at length FD is selected on the basis of the extent of distal stem support within the isthmus sector or below, as required. The distal stem length FD generally is approximately 40 mm to 60 mm long and can exceed 300 mm in length in some special situations where additional stem and/or femoral bone support is surgically indicated. The size or diameter of the distal stem D is a selected dimensional parameter and generally is within the range of 7 mm to 15 mm, with an average of, for example, 11 mm for a Japanese patient and within a larger range of approximately 10 mm to 20 mm, at an average value of approximately 13-14 mm, for Western European and North American patients. The proximal length FP of the medullary stem originates at the level of the medial collar and terminates at the origin of the distal portion of the stem. Generally, the proximal stem length FP ranges from approximately 50 mm to 70 mm, depending upon physiological and pathologically related factors. The length l of neck 34 of femoral component 30 is less related to femur physiology than upon sexual and pathological differences. The nominal neck length 11, 12 and 13, defined as the dimension from the distal side of the collar 40 to the head center C1, C2 or C3, generally ranges from 27 mm to 30 mm, with lengths of 12 mm or more additionally being added by using femoral head components 36, which are assembled onto a locking Morse taper connection 38 located at the proximal end of neck 34. H1, H2 and H3 in FIG. 3A represent the horizontal off-set distances for stems 32, 132 and 232, respectively.

Figure 5:
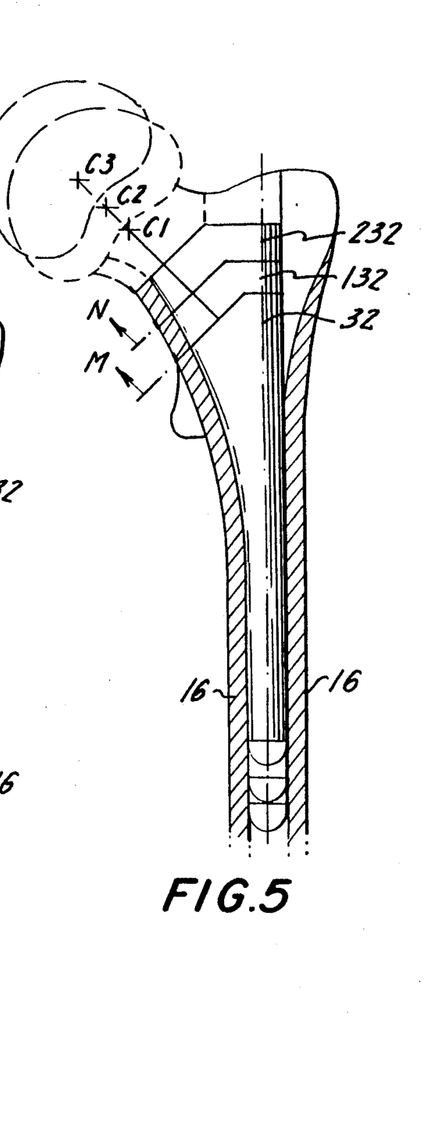
FIG. 5 is an anterior elevational view, taken along the anterior-posterior plane, showing the three femoral prosthesis components of FIG. 3A superimposed upon each other and mounted in a femur at different seated levels.

Thus, with the present invention, there is a constant radius of curvature R for intramedullary stems 32, 132 and 232 having different proximal widths P1, P2 and P3 at a given distal stem diameter D, to define the proximal-medial curvature or shape. By providing the same radius of curvature R, the surgeon can apply an array of femoral components to accurately fit within the medullary canal of different proximally sized femurs of identical distal diameters D, as shown in FIGS. 4A-4C. The present invention also provides the ability to be applied to the medullary canal at the same stem/bone fit within a given femur of given distal diameter D, as shown in FIG. 5. The latter aspect is possible since the stems of the femoral components incorporate the same radius of curvature R, proximal-medially, at a given distal diameter, and therefore, are capable of being applied to the same femur. In other words, the same medullary canal in the femur can fit any of the three different stems 32, 132 and 232 with the same intramedullary fit, because the stems have the same radius of curvature R. However, the different stems 32, 132 and 232 will seat at different levels within the femur, as shown best in FIGS. 3B, 3C and 5. Therefore, because the same radius of curvature R is provided and the same distal diameter D is provided for stems 32, 132 and 232, in addition to fitting the bone easily and exactly for all stems, the head centers C1, C2 or C3 can be selected for the particular patient to obtain the desired duplication of hip joint biomechanics.

Further, in many cases, there is a bone loss medially in the proximal femoral bone, that is, at levels M and N of FIG. 5. With the present invention, variation of proximal intramedullary stem widths P1, P2 or P3 can be effectively utilized to compensate for this proximal femoral bone loss, while still achieving the same level of intramedullary stem fit. In such cases, a head extension can be added to bring the head back up to the appropriate position. Thus, the same canal preparation can be used.

As aforementioned, the present invention also provides a greater flexibility to the surgeon for duplicating the biomechanical characteristics of the patient's hip joint. Thus, the nominal head centers C1, C2 and C3 for the femoral components of a given set of proximal widths P1, P2 and P3 at a given distal diameter D can be designed to provide an alignment or complementary pattern of center positions denoted by points C1, C2 and C3 in FIG. 3B, within a tolerance band 50, to address a linear pattern of hip joint articular centers within a clinically acceptable tolerance band. Alternatively, it can be designed to provide an array or scattered pattern of nominal head centers to address a wider range of head center distribution as noted at points C1', C2' and C3' of FIG. 3C, within a tolerance band 52.

Thus, with the present invention, as shown best in FIGS. 3B, 3C and 5, the medial sides of the femoral components are in exact alignment only when the stems are offset in the lengthwise direction from each other, thereby providing the exact same fit within the femur while also allowing different positions of the articular center C of the hip joint. Thus, the same femoral canal preparation can accommodate three different stems to obtain three different head center positions. Additionally, the stems can be exactly implanted into femurs of different physiological proximal-transverse size and of similar distal canal size.

In addition to the aforementioned advantages, the instrumentation design is reduced to a singular rasp for preparing the proximal-medial canal for each distal bore size, and therefore reducing the total number of instruments required. Because of the different radii of curvature for the different femoral components according to the prior art, the number of instruments required to accommodate each distal size of femoral bone is large. In addition, after the bone is prepared for a particular stem according to the prior art, another stem of different proximal-transverse size cannot be easily interchanged therewith without requiring additional bone preparation or resulting in less desirable stem/bone interface conformity.

As still another advantage, the manufacturing of the stems according to the present invention is simplified over the prior art because the number of casting patterns required to generate the three stem shapes can be accommodated by a single pattern per distal stem size and similarly, any machining processes require only a single nesting fixture. This is a result of the same radius of curvature R for stems of consistent distal stem diameter, and results in a large cost savings in the manufacture of the components.

Although the present invention has been described with respect to a straight stem in the lateral view, it is possible to use the present invention with a curved stem in the lateral view. Such modification is encompassed within the scope of the present claimed invention.

Having described a specific preferred embodiment of the invention with reference to the accompanying drawings, it will be appreciated that the present invention is not limited to that precise embodiment, and various changes and modifications can be effected therein without departing from the scope or spirit of the invention as defined by the appended claims.

What is claimed is:

1. A system of femoral components for a hip joint prosthesis, comprising:
   an intramedullary stem for each femoral component, each stem having a distal end, a proximal end, a lateral side extending between said distal and proximal ends, and a medial side extending between said distal and proximal ends opposite to said lateral side, said medial side having a concave curvature;

a femoral ball component mounted at said proximal end of each said stem, each said femoral ball component having an articular center; and the medial sides of at least two of said stems substantially being in exact alignment only when the stems are offset in the lengthwise direction from each other, thereby permitting different positions of the articular centers of the femoral ball components.

2. A system according to claim 1 wherein each femoral component further includes a neck portion for connecting the femoral ball component to the proximal end of the intramedullary stem thereof.

3. A system according to claim 1 wherein the distal end of each said intramedullary stem has a circular cross-sectional configuration with a distal diameter, and the distal diameters of the intramedullary stems are identical.

4. A system according to claim 1 wherein the medial sides of all of said stems are substantially in exact alignment only when the stems are offset in the lengthwise direction from each other.

5. A system according to claim 1 wherein the proximal end of each intramedullary stem has a proximal width, and the proximal width of each intramedullary stem is different from the proximal width of the other intramedullary stems.

6. A system according to claim 1 wherein the medial sides at the proximal ends of the stems have the same radius of curvature.

7. A system of femoral components for a hip joint prosthesis, comprising:

an intramedullary stem for each femoral component, each stem having a distal end, a proximal end, a lateral side extending between said distal and proximal ends, and a medial side extending between said distal and proximal ends opposite to said lateral side, said medial side having a concave curvature;

the distal end of each said intramedullary stem having a circular cross-sectional configuration with a distal diameter, and the distal diameters of the intramedullary stems being identical;

the proximal end of each said intramedullary stem having a proximal width, and the proximal width of each intramedullary stem being different from the proximal width of the other intramedullary stems;

a femoral ball component for each femoral component, each said femoral ball component having an articular center;

a neck portion for connecting the femoral ball component to the proximal end of the intramedullary stem thereof; and the medial sides at the proximal ends of the stems have the same radius of curvature, such that the medial sides of all of said stems substantially are in exact alignment only when the stems are offset in the lengthwise direction from each other, thereby permitting different positions of the articular centers of the femoral ball components.

8. A system of femoral components for a hip joint prosthesis, comprising:

an intramedullary stem for each femoral component, each stem having a distal end, a proximal end, a lateral side extending between said distal and proximal ends, and a medial side extending between said distal and proximal ends opposite to said lateral sides, said medial side having a concave curvature;

a femoral ball component mounted at said proximal end of each said stem, each said femoral ball component having an articular center; and the medial sides at the proximal ends of, at least two of the stems have centers of curvature and the same radius of curvature, with said centers of curvature of the medial sides of said at least two stems being displaced with respect to each other for a given distal diameter.

9. A system according to claim 8 wherein each femoral component further includes a neck portion for connecting the femoral ball component to the proximal end of the intramedullary stem thereof.

10. A system according to claim 8 wherein the distal end of each said intramedullary stem has a circular cross-sectional configuration with a distal diameter, and the distal diameters of the intramedullary stems are identical.

11. A system according to claim 8 wherein the medial sides of all of said stems are substantially in exact alignment only when the stems are offset in the lengthwise direction from each other.

12. A system according to claim 8 wherein the proximal end of each intramedullary stem has a proximal width, and the proximal width of each intramedullary stem is different from the proximal width of the other intramedullary stems..

13. A system according to claim 8 wherein the medial sides at the proximal ends of the stems have the same radius of curvature.

* * * * *